(12) United States Patent
Barbarash et al.

(10) Patent No.: US 7,014,655 B2
(45) Date of Patent: Mar. 21, 2006

(54) METHOD FOR CONSERVING BIOLOGICAL PROSTHESES, CONSERVED BIOLOGICAL PROSTHESES AND CONSERVING SOLUTIONS (75) Inventors: Leonid Barbarash, Kemerovo (RU); Irina Jouravleva, Kemerovo (RU); Svetlana Novikova, Moscow (RU)

(73) Assignees: Rainer Frey, Starnberg (DE); Gerhard Wachauf, Munich (DE)

(*) Notice: Subject to any disclaimer, the term of this patent is extended or adjusted under 35 U.S.C. 154(b) by 2 days.

(21) Appl. No.: 10/433,872

(22) PCT Filed: Dec. 3, 2001

(86) PCT No.: PCT/DE01/04494

§ 371 (c)(1),
(2), (4) Date: Mar. 1, 2004

(87) PCT Pub. No.: WO02/058745

PCT Pub. Date: Aug. 1, 2002

(65) Prior Publication Data

US 2004/0136965 A1    Jul. 15, 2004

(30) Foreign Application Priority Data

Dec. 3, 2001    (DE) .............................. 100 60 660

(51) Int. Cl.
*A61F 2/24* (2006.01)

(52) U.S. Cl. .................. 623/2.13; 623/2.1; 623/11.11; 424/569; 424/570; 514/56; 514/165; 514/723

(58) Field of Classification Search ............... 623/2.1, 623/2.13, 11.11; 514/56, 165, 723; 424/569, 424/570

See application file for complete search history.

(56) References Cited

U.S. PATENT DOCUMENTS

| 5,080,670 A |   | 1/1992 | Imamura et al. ............... 623/2 |
| 5,165,919 A |   | 11/1992 | Sasaki et al. ............... 424/488 |
| 5,880,242 A | * | 3/1999 | Hu et al. ..................... 527/200 |

FOREIGN PATENT DOCUMENTS

| WO | WO92/09309 |   | 6/1992 |
| WO | WO 9209309 A2 | * | 6/1992 |
| WO | WO97/32472 |   | 9/1997 |
| WO | WO 9732472 A1 | * | 9/1997 |
| WO | WO98/46288 |   | 10/1998 |

OTHER PUBLICATIONS

Anonymous, "ISIS-3: a randomised comparison of streptokinase vs tissue plasminogen activator vs anistreplase and of aspirin plus heparin vs aspirin alone among 41,299 cases of suspected acute myocardial infarction," The Lancet 339 (8796):753-770, 1992.*

(Continued)

*Primary Examiner*—Robert A. Wax
*Assistant Examiner*—Rosanne Kosson
(74) *Attorney, Agent, or Firm*—Elliot M. Olstein; Raymond J. Lillie (57) ABSTRACT

The invention concerns a method of conserving biological prostheses, wherein the method includes the following steps: (a) treating biological prostheses with a solution which contains a mixture of epoxide compounds which are at least in part of different lengths; (b) treating the biological prosthesis treated in accordance with step (a) with an antithrombotic-bearing solution; and (c) possibly storing the prosthesis treated in accordance with step (b) in a sterilising solution. The invention further concerns a biological prosthesis produced in accordance with the method of the invention and a conserving agent.

26 Claims, 1 Drawing Sheet

OTHER PUBLICATIONS

Lohre, et al., *ASAIO Journal*, vol. 39, No. 2, pp. 106-113 (Apr. 1993).

Chanda, et al., *Biometerials*, vol. 19, pp. 1651-1656 (1998).
Schmidt, et al., *Biomaterials*, vol. 21, pp. 2215-2231 (2000).

* cited by examiner

FIG. 1

METHOD FOR CONSERVING BIOLOGICAL PROSTHESES, CONSERVED BIOLOGICAL PROSTHESES AND CONSERVING SOLUTIONS

The invention concerns a method of conserving biological prostheses and biological prostheses produced in accordance with that method. The invention further concerns a conserving solution for conserving biological prostheses.

Biological prostheses can be produced from body components of human beings and animals. For example heart valves, arteries etc of cattle or pigs are used as implants in human beings.

It will be appreciated that the biological prostheses must be chemically treated prior to implantation in the organism of the human being. The treatment method must ensure:

1) the absence of immunogenity (that applies equally to heterologous and allogenous tissue);
2) sterility of the implant;
3) high strength, elasticity and deformation properties of the biological material; and
4) high biocompatibility whose main parameter, in relation to the biological prostheses, is the absence of calcification and thromboses in the event of long-term use in the recipient organism.

For more than 30 years now glutaraldehyde has represented the main conserving agent for cardiac-circulatory bioprostheses (biological prostheses). Glutaraldehyde reacts with the amino groups of lysine and hydroxylysine. As a result of those reactions, chemical bonds are formed, which are represented in particular by Schiff's bases or pyridine bases. Glutaraldehyde ensures reliable sterility and the suppression of antigenic properties of the biological material.

Glutaraldehyde however makes the tissue stiff and hydrophobic and the surface assumes a rough disordered relief. In addition the chemical compounds of glutaraldehyde and collagen have in their structure ligands for complex formation with calcium cations. Those complexes do in fact subsequently become centers of hydroxyapatite crystallisation. In overall terms the result of this is that the glutaraldehyde has a negative influence on the thrombosis-resistant properties of the tissue and gives rise to calcification of the biological materials.

In order to eliminate the negative influence of glutaldehyde on the biological material, methods have been developed for the additional chemical modification of biological prostheses.

For increasing thrombosis resistance use was made for example of heparin (U.S. Pat. No. 3,988,782) while aminodiphosphonates were used for the prophylaxis of calcification (U.S. Pat. No. 4,553,974). However those methods do not have the expected effect as the negative influence of the glutaraldehyde as a main conserving agent on the tissue is excessively great.

A greater effect can be achieved by replacing the main conserving agent by a cross-linking agent, the structural formula of which does not contain any aldehyde group.

Methods are known for conserving biological prostheses using individual polymer (U.S. Pat. No. 4,806,595 and U.S. Pat. No. 5,080,670) and non-polymer (U.S. Pat. No. 5,880,242 and RU 2 008 767) epoxide compounds.

Epoxide compounds are effective cross-linking agents, guarantee strength and elasticity of the biological material, inhibit calcification of the biological prostheses and have pronounced antigen-depressive properties.

To improve the thrombosis resistance of the tissue, it is possible to implement an additional modification with heparin (U.S. Pat. No. 4,806,595 and RU 2 008 767). The disadvantages of those methods are as follows:

1) A masking effect which is characteristic of non-polymer or polymer di-epoxides when one of the epoxy groups reacts with collagen but the other remains without a bond, that is to say it does not react. On the one hand those unbound, that is to say free epoxy groups exhibit a cytotoxic effect, on the other hand they result in insufficient density in terms of transverse cross-linking, which has a negative influence on the strength properties of the tissue.

2) The use of individual polymer epoxides, in the structural formula of which there are contained more than two epoxide groups, reduces the masking effect but it detrimentally affects transverse cross-linking and increases the content of free epoxide groups in the tissue. Without an additional modification which is targeted at closing or converting those groups, on the one hand the cytotoxic effect is increased. On the other hand the number of such epoxide groups is too low for saturation of the biological material with substances which impart additional properties to the biological prostheses (heparin, anti-bacterial agents and so forth).

The method known from U.S. Pat. No. 4,806,595 for heparin treatment of epoxy-conserved biological prostheses includes the use of protamine which is firmly bound to the collagen by an epoxide bond. The procedure involves in turn fixing on the protamine heparin which, lifting off the surface, exerts an anti-coagulant function.

The effectiveness of such a method is however limited in respect of time and requires the use of an intermediate reagent, namely protamine. The possibility of bonding protamine to the collagen—if this is involves collagen from the bonding tissue of the biological prosthesis—is in turn limited by the number of free reactive groups of the conserving agent as the main proportion of those groups is required for the cross-linking effect.

U.S. Pat. No. 5,165,919 discloses a method of covalent fixing of heparin on medical implants by the interaction of amino and epoxy groups. That method however was developed for polymer materials and cannot be used for biological prostheses.

The object of the invention is to provide a method of conserving biological prostheses which are resistant to calcification and thrombosis formation and have an enhanced level of strength and elasticity. Another object of the invention is to provide improved conserved biological prostheses.

In accordance with the invention preferably mixtures of polymer and non-polymer epoxide compounds are used for conserving biological prostheses, wherein 2 and more epoxide groups are present in the structural formula of the epoxide compounds.

Preferably a solution with a mixture of at least three different epoxide compounds (components) is used.

In a further preferred feature the antithrombotic is selected from the group which consists of heparin, low-molecular heparin, heparinoids, hirudin and mixtures thereof.

It is essential in accordance with the invention that the antithrombotic has antithrombotic or anti-coagulating properties. In that respect it is possible in accordance with the invention to use all substances which have a heparin-like action.

Thus it is also possible to use chemically, mechanically and/or enzymatically modified heparin, truncated heparin, recombinant heparin or mixtures thereof insofar as the correspondingly modified heparin has antithrombotic properties.

Preferably heparin is used in accordance with the invention.

It was surprisingly found that:

1) the strength of the biological prosthesis is increased by transverse connections as the accessibility of reactive groups of collagen in the biological prosthesis for an interaction with various conserving agents which have various molecule lengths is guaranteed. That enhances the strength of the biological material and ensures a better antigen depression effect;

2) the use of compounds with more than 2 epoxide groups in the mixture of epoxide compounds permits the production of biological material with a predetermined number of free epoxy groups;

3) subsequently heparin can be immobilised on those groups to impart thrombosis resistance. Immobilisation of heparin in the complex with acetylsalicylic acid strengthens the thrombosis-resistance effect.

After conservation and modification with heparin the biological prostheses produced in that way can be stored in a solution of any compound which guarantees sterility. Preferably epoxide compounds are used in order to avoid possible additional chemical reactions.

The subject-matter of the present invention is thus on the one hand a method of conserving biological material which can be used in particular for producing heart and blood vessel valve prostheses. On the other hand the subject-matter of the invention is the provision of the biological prostheses which are conserved in accordance with the method of the invention.

In accordance with the invention, preferably to provide the conserving effect instead of individual epoxide conserving agents, mixtures of polymer and non-polymer epoxide compounds with a differing number of epoxide groups (2 and more) are used. The composition of the mixture can be varied in dependence on the nature of the biological material and the aims of a subsequent chemical modification.

Preferably the epoxide group in the epoxide compounds used is a constituent of a glycidol residue.

In order at the same time to improve the thrombosis-resistance properties and to close, that is to say transform, the free epoxide groups which have not bound to the collagen in the conservation procedure subsequent treatment of the biological material with heparin and acetylsalicylic acid is implemented.

Preferably a mixture of polymer and non-polymer epoxide compounds is used for conserving heart-circulatory bioprostheses (bioprosthesis—biological prosthesis).

In accordance with the invention the term a polymer epoxide compound is used to identify an epoxide compound which is composed of at least two repetitive, directly interconnected units to which epoxy group-bearing residues such as for example glycidol or 2,3-epoxypropan-1-ol are joined.

Preferably the polymer epoxide compounds have a degree of polymerisation of at least two, more preferably between three and 25, still more preferably between three and 15, in particular between four and nine. In this respect the degree of polymerisation relates to the polymer proportion of the epoxide compound, bearing the epoxy groups.

Instead of a polymer epoxide compound it is also possible to use an epoxide compound with between two and three epoxide groups, wherein arranged between at least two epoxide groups is a straight-chain or branched hydrocarbon chain with at least four carbon atoms, for example a tetramethylene group. Preferably arranged between the at least two epoxide groups is a straight-chain or branched hydrocarbon chain with at least six, preferably six, carbon atoms, such as for example a hexamethylene group.

In accordance with the invention the term non-polar epoxide compound is used to identify an epoxide compound which does not have any repetitive, directly interconnected units to which epoxy group-bearing residues such as for example glycidol or 2,3-epoxypropan-1-ol are joined.

It may be advantageous to vary the composition of the mixture in dependence on the association in respect of nature and tissue of the biological material. That is related to the spatial configuration and the composition of the collagens of the various tissues and the different accessibility of the reactive amino acid groups of the collagen for the conserving agents which have different structural formulae.

In addition the composition of the mixture depends on the purpose of the additional chemical modification; saturation of the biological material with a predetermined number of epoxide groups which are required for covalent immobilisation of biologically active substances is possible. Thus for example upon immobilisation of heparin a large number of epoxide groups is required.

For that purpose the mixture is preferably adjusted as follows:

40–80% by weight, more preferably 50–70% by weight, of at least one non-polymer epoxide compound with two epoxide groups;

5–20% by weight, more preferably 10–15% by weight, of at least one polymer epoxide compound with between two and three epoxide groups and/or at least one epoxide compound with between two and three epoxide groups, wherein arranged between at least two epoxide groups is a straight-chain or branched hydrocarbon chain with at least four carbon atoms; and 15–45% by weight, more preferably 20–35% by weight, of at least one epoxide compound with at least three epoxide groups;

wherein the total amount is 100% by weight. The foregoing percentage details of the respective epoxide compound in percent by weight relate in each case to the total amount of epoxide compounds used.

In a modification of high-molecular polymer substances in contrast the number of reactive groups must be low as supersaturation of the tissue of the biological prosthesis with high-molecular polymers results in an impairment of the properties in respect of elasticity and deformation. Accordingly use of the epoxide mixtures of differing composition permits the amount of substance which is immobilised on the biological material to be controlled or influenced.

For that purpose the mixture is preferably adjusted as follows:

70–90% by weight, more preferably 75–85% by weight, of at least one non-polymer epoxide compound with two epoxide groups;

5–20% by weight, more preferably 10–15% by weight, of at least one polymer epoxide compound with between two and three epoxide groups and/or at least one epoxide compound with between two and three epoxide groups, wherein arranged between at least two epoxide groups is a straight-chain or branched hydrocarbon chain with at least four carbon atoms; and up to 5% by weight, more preferably 1–2% by weight, of at least one epoxide compound with at least three epoxide groups;

wherein the total amount is 100% by weight. The foregoing percentage details of the respective epoxide compound in percent by weight relate in each case to the total amount of epoxide compounds used.

In the case of the above-specified mixtures a non-polymer, preferably low-molecular compound, with two reaction groups, must be present in the mixture. For example it is possible to use alkane diol diglycidylether such as for example butane-1,4-diol diglycidylether, polyalcohol diglycidylether such as for example glycerine diglycidylether, alkylene glycol diglycidylether such as ethylene glycol diglycidylether or mixtures thereof. Preferably ethylene glycol diglycidylether is used.

Those compounds ensure intermolecular transverse cross-linking of the collagen and intramolecular cross-linking of proteoglycans and proteins of the cell elements which represent the most active antigenic determinants.

The concentration of non-polymer epoxide compound with two epoxide groups (di-epoxide compound) in the mixture is preferably 1–95% by weight, more preferably 20–90% by weight. Very good results were obtained with a concentration of 40–80% by weight.

The second component in the mixture is a polymer epoxide compound which contains between two and three epoxide groups in the structural formula and/or an epoxide compound with between two and three epoxide groups, wherein arranged between at least two epoxide groups is a straight-chain or branched hydrocarbon chain with at least four carbon atoms.

For example it is possible to use polyalkylene glycol diglycidylethers such as for example polyethylene glycol diglycidylether, polytetramethylene glycol diglycidylether, polypropylene glycol diglycidylether or mixtures thereof.

Instead of or in addition to the above-noted polymer epoxide compound it is also possible to use alkane diol diglycidylethers such as for example hexane-1,6-diol diglycidylether and/or higher dicarboxylic acid diglycidylesters.

In accordance with the invention the term higher dicarboxylic acid diglycidylester is used to identify glycidol esterified with higher dicarboxylic acids (2,3-epoxypropan-1-ol), that is to say diglycidylesters of higher dicarboxylic acids. Identified as higher dicarboxylic acids are those which have more than 12 carbon atoms.

By way of example higher dicarboxylic acid diglycidylesters which can be used are Denacol EX-1111 (mixture of two acids with a molecular weight of 398 g/mol and 454 g/mol) or Denacol EX-1112 (mixture of two acids with the same molecular weight of 450 g/mol but of differing structure) from Nagase Company Ltd, Japan.

Preferably polyethylene glycol diglycidylether is used. Preferably the polyethylene glycol diglycidylether has a degree of polymerisation of 3–12, more preferably 4–9.

That component supplements cross-linking of the collagen by inter-fibrillar bonds. The concentration in the mixture is preferably 1–95%, more preferably 2–40% by weight, still more preferably 5–20% by weight.

The third component is an epoxide compound with a number of epoxide groups of at least three, for example four, five or more.

Preferably in that respect polyalcohol polyglycidylethers are used such as for example sorbitol polyglycidylether, glycerine polyglycidylether and the like, polysaccharide polyglycidylether or mixtures thereof. Preferably pentaerythrol polyglycidylether is used.

That third component saturates the tissue with an optimum number of free epoxide groups, to which heparin can be immobilised without the use of additional reagents. The concentration of the component in the mixture is preferably 1–95% by weight, more preferably 10–50% by weight. Very good results were obtained with a concentration of 15–35% by weight.

The foregoing percentage details of the respective epoxide compound in percent by weight relate respectively to the total amount of epoxide compounds used.

The method according to the invention permits an increase in the density of cross-linking of the collagen, which has an advantageous effect on the strength properties of the biological prosthesis. The use of mixtures of polymer and non-polymer epoxides imparts to the biological material a higher level of resistance to calcification.

Saturation of the tissue with free epoxide groups makes it possible to implement covalent immobilisation of heparin on the biological prosthesis when pre-treated in that way.

In relation to the functional groups of the heparin, the epoxy group represents one of the most reactive groups in the polymers, including also in biological materials. Binding of the heparin by way of the amino group does not have a disadvantageous effect on the anti-coagulant properties thereof.

Reaction with the epoxy group makes it possible to implement immobilisation of heparin under 'gentle' conditions which exclude unwanted physical-chemical changes in the biological material. Reaction of heparin with the epoxy groups can take place in a wide pH-range of the medium (pH 2–11).

In terms of modification of the biological tissue, preferably a pH-value of 5–8 is used, for example employing phosphate buffers, phosphate-citrate buffers and/or acetylsalicylic acid.

Such an operating procedure makes it possible on the one hand to achieve an improvement in the thrombosis-resistant properties and on the other hand to neutralise the free epoxy groups which are always present in the biological material as a result of the masking effect.

The introduction of a third component, that is to say a compound with a number of epoxy groups of at least 3, into the epoxide conserving agent makes it possible to increase the amount of immobilised heparin. The covalently bound, that is to say immobilised heparin does not pass into the bloodstream but has an antithrombotic effect due to binding and sorption to the protein layers and smoothing of the surface of the biological prosthesis.

The use of acetylsalicylic acid for setting an acid pH-value in the immobilisation of heparin surprisingly further increases the thrombosis resistance of the surface.

To produce a conserved biological prosthesis according to the invention for heart-circulation surgery, such as for example biological heart valve prostheses, it is possible to use for example aorta complexes of a pig or pericardia of cattle. In the case of arteriosclerosis for example damaged arteries can be replaced by the internal thoracic artery or the head artery of cattle.

Allogenous or heterologous mitral valves or tricuspidal valves can be used for the orthotopic replacement of heart valves. For intracardial plastic surgery and angioplastic surgery it is possible to use pericardia from cattle, the allogenous hard meninges or body-specific pericardia. Valves, membrane-like tissues and vessels, for example arteries, veins, artery segments, vein segments and so forth can be taken from any biological genuses of mammals, for example cattle, pigs, sheep, human beings and so forth, insofar as they are suitable in respect of their anatomical features for replacement of one element or another of the heart-circulation system.

Examples 1 through 3 according to the invention which are set out hereinafter serve only to further illustrate the invention and in no way limit the scope of protection thereof.

In the examples according to the invention a mixture of ethylene glycol diglycidylether (DEE), pentaerythrol polyglycidylether and polyethylene glycol diglycidylether were used in the respectively specified quantitative ratios for conservation of the respective biological prosthesis used.

In that respect the examples were all implemented at ambient temperature, that is to say at between about 20° C. and about 25° C. It is also possible to use higher temperatures, but not more than 37° C. In all incubation steps, the solutions were not agitated. It will be appreciated however that the solutions can also be agitated.

EXAMPLE 1 ACCORDING TO THE INVENTION

Aortic valve vela of a pig (15 g of moist tissue) were rinsed with 0.9% by weight NaCl solution and put into 200 ml of a conserving solution according to the invention, which is produced from 50 mM phosphate buffer pH 7.4 and contains 6 g of ethylene glycol diglycidylether, 1 g of polyethylene glycol diglycidylether (n=5) and 3 g of pentaerythrol polyglycidylether (number of glycidylether units per molecule: 4).

After 48 hours the conserving solution was replaced by an identical but freshly produced solution. After 12 days the valve vela were rinsed with sterile 0.9% by weight NaCl solution and incubated in a heparin solution (100 IU/ml, IU: International Unit) pH 5.0, in which case the pH-value was adjusted by the addition of aqueous acetylsalicylic acid solution, for a period of 3 hours at a temperature of 20° C.

Thereafter rinsing was effected five times with an excess of 0.9% by weight NaCl solution and the treated valve vela were put into 5% by weight ethylene glycol diglycidylether solution where they were stored until further use.

Production of the heparin solution

The ratio of heparin: acetylsalicylic acid in the heparin solution, in relation to weight, is about 1.3–16:1. The precise ratio of heparin: acetylsalicylic acid depends on the respective activity (in IU/weight) of the heparin used.

By way of example a heparin solution which is suitable for the invention can be produced by the addition of about 7–10 mg/ml of acetylsalicylic acid to a heparin solution with about 75–100 IU/ml. In that case acetylsalicylic acid is added to the heparin solution until the pH-value of the solution is between about 5 and 6. The concentration of the heparin solution is at least 75 IU/ml, preferably 100 IU/ml. It will be appreciated that it is also possible to use solutions with higher heparin concentrations.

COMPARATIVE EXAMPLES 1

Comparative samples involved using aortic valve vela of a pig, which were treated with 0.625% by weight glutaraldehyde (GA) in 50 mM phosphate buffer pH 7.4 or with 5% by weight ethylene glycol diglycidylether (DEE) and 100 IU/ml heparin in 50 mM phosphate buffer pH 7.4 (DEE+heparin) (see RU 2 008 767).

a) Treatment of Samples with Glutaraldehyde

The comparative samples were incubated for 28 days in 0.625% by weight glutaraldehyde (GA), and 50 mM phosphate buffer pH 7.4 at ambient temperature (between 20° C. and 25° C.). The GA-solution was changed four times, that is to say after the 1st, 3rd, 7th and 21st days. Prior to further use (analysis or implantation) the conserving solution was removed. Subsequently the comparative sample was washed at ambient temperature for one hour without agitation in 0.9% common salt solution. The common salt solution was changed in that procedure after every 20 minutes (a total of three washing steps).

b) Treatment of Samples with DEE and Heparin

The comparative sample was incubated for 21 days in 5% by weight ethylene glycol diglycidylether (DEE) and 50 mM phosphate buffer pH 7.4 at ambient temperature (20° C.–25° C.). The DEE solution was changed after three days without a washing step. The conserving solution was then removed. The comparative sample was then washed at ambient temperature for one hour without agitation in 0.9% common salt solution. In that procedure the common salt solution was changed after every 20 minutes (a total of three washing steps). The heparin treatment was effected with 100 IU/ml at 37° C. for 8–16 hours. The unbound heparin was removed by washing with 0.9% by weight common salt solution for one hour at ambient temperature (20–25° C.). During the washing operation the common salt solution was not agitated and not changed. The comparative sample was stored in 2–5% by weight DEE solution. The conserving solution was removed prior to further use (analysis or implantation). The comparative example was then washed at ambient temperature for one hour without agitation in 0.9% common salt solution. In that procedure the common salt solution was changed after every 20 minutes (a total of three washing steps).

Comparison of Examples According to the Invention and Comparative Examples

The improvement in the properties of biological prostheses conserved using the method according to the invention (Examples 1 through 3 according to the invention) is clearly shown by comparison of biological prostheses conserved with conventional conservation methods (comparative Examples 1 through 3). In that respect the density of transverse cross-linking of amino acids in the respective biological prostheses used, the properties in respect of elasticity and deformation, the degree of calcification and the amount of immobilised heparin were determined and compared to each other.

The above-indicated parameters were determined in that respect in the following fashion.

Determining Transverse Cross-Linking

The density of transverse cross-linking was assessed in accordance with the reduction in the number of free amino acid residues in the biological material, in which respect they were determined by an amino acid analysis method.

For the amino acid analysis procedure, five samples were taken in each case and washed with distilled water which was renewed twice in one hour. The samples were then lyophilised for three hours (temperature of the sample: between −55° C. and +60° C.). Between 1.5 and 2 mg of dry tissue was put into between 0.15 ml and 2 ml of 6 N HCl and incubated in sealed vacuum flasks for 24 hours at 110° C. Thereafter the acid was evaporated and the residue was diluted in 2.5 ml of lithium citrate buffer and centrifuged. The supernatant substance was subjected to an amino acid analysis operation in an amino acid analyser (CL 5001 BIOTRONIC, Germany) with computer-aided data evaluation (CR-3A, SHIMADZU Integrator, Japan).

Determining the Properties in Respect of Elasticity and Deformation

The samples were cut out in dumbbell shape (dumbbell test bodies) using an especially shaped blade. That blade is of a standard shape and size and has sharpened edges. Using that blade, samples of a standardised size are cut out of the biological material. Ten samples were investigated in each case.

The properties in respect of elasticity and deformation were determined on the tensile strength testing machine 'Instron-1122' (manufacturer: INSTRON, England).

All the materials investigated were loaded to investigate the breaking/tearing strength at a constant speed (50 mm/min).

The average thickness h of the samples (mm) was determined using a micrometer eyepiece.

The data were calculated as follows:

a) Maximum tensile strength (tensile stress) $\sigma$ (kg/cm$^2$)

$\sigma = P_{max}/S$, wherein $P_{max}$ is the breaking load (kg) and S is the cross-sectional area of the sample (cm$^2$), $S = h \times b_0$, wherein h (cm) is the thickness of the sample and $b_0$ (cm) is the width of the sample.

In the present case the width of the sample was set to 0.25 cm using the above-mentioned blade.

b) Maximum stretch $\epsilon_{max}$ (%)

$\epsilon_{max} = (\Delta I_{max}/I_0) \times 100$, $\Delta I_{max} = I_{max} - I_0$, wherein '$I_{max}$' is the final length and '$I_0$' is the initial length of the sample.

In the present case the samples were of an initial length of 11 mm.

Determining Calcification

Resistance to calcification was investigated by subcutaneous implantation of conserved biological prostheses under the skin of 3-week male rats (diameter of the samples: 7 mm).

Three samples, in each case one of the biological samples conserved using GA, DEE+heparin and the conserving solution according to the invention, were each implanted into a respective one of male Vistar rats (n=33), weight 48.64±3.5 g, under ether anesthesia. The implants were removed from 11 animals in each case after a respective period of 30, 60 and 90 days.

After removal of the samples they were cleaned of the surrounding tissue, washed with 0.9% NaCl solution and dried at 56° C. for a day. Then each of the samples was hydrolysed in concentrated chloric acid. The samples were then quantitatively investigated for calcium by means of atom absorption spectroscopy.

Determining the Amount of Immobilised Heparin

The amount of immobilised heparin was determined by means of elementary analysis in accordance with the difference in the content of sulfur in unmodified (control sample) and modified sample portions (modified sample).

The method is based on determining the difference in the level of sulfur concentration in test samples (modified sample) and control samples. The sulfur content in heparin is high and low in collagen. A rise in the sulfur content after modification of the biological prosthesis accordingly permits calculation of the amount of heparin immobilised to the biological prosthesis.

$\Delta$[S]heparin=[S]mod. sample–[S]control sample, wherein [S] is the sulfur concentration in [$\mu$g/g] dry weight.

In that respect calculation of the heparin content in the sample is effected in accordance with the following formula:

$Y = \Delta[S]/S_1$, wherein Y is the heparin content in the biological material (biological prosthesis) in [mg/g], $S_1$ is the sulfur content in [$\mu$g] in 1 mg of heparin.

Basically any quantitative determination method can be used for determining the concentration of the sulfur content.

In the present case the determination procedure was effected as follows:

The method of determining the concentration of the sulfur—which is contained in the range of between 0.2 and 100% in organic samples—is based on the titration of an aqueous-organic medium after combustion of the sample in an oxygen-bearing flask.

The sample material (at least 20 g) is firstly cut up with a pair of shears until a thin pulpy consistency is attained. Each sample has 10 ml of distilled water poured thereover. The sample is frozen at –55° C. and lyophilised with a stepwise increase in temperature to, +60° C. until dry. The dried sample material obtained in that way is finely ground in an agate mortar until a fine powder is produced.

5 mg of the sample material is weighed out on an analytical balance with a graduation of 0.0001 g. The weighed sample is burnt in a flask which is filled with gaseous oxygen and contains 10 ml of 6% $H_2O_2$ solution. After the burning operation the combustion products are rinsed with 5 ml of water and cooled. Added to that solution are 0.25 ml of 2 N HCl, 25 ml of acetone and 2 drops of indicator (0.2% aqueous chlorophosphonazo-III solution (bis-(4-chloro-2-phophonobenzolazo)-2,7-chromotropic acid, Fluka Chemie AG, CH-9471 Buchs, Switzerland). Titration is effected with 0.02 N Ba(NO$_3$)$_2$ solution until there is a transition from a violet-rose coloration to a light blue coloration. For control purposes a blind test is carried out under analysis conditions including combustion and titration.

The sulfur content X is calculated as follows:

$$X = \frac{(V - V_0) \times K}{A} \times 1000,$$

wherein:

V is the volume of 0.02 N Ba(NO$_3$)$_2$ solution in [ml], which is used for the titration procedure, $V_0$ is the volume of 0.02 N Ba(NO$_3$)$_2$ solution in [ml], which is used for the titration procedure in the blind test, K is the conversion factor which reproduces the titer of the Ba(NO$_3$)$_2$ solution for the sulfur equivalent in [mg/ml], and A is the weight of the sample in [mg].

It will be appreciated that the amount of immobilised heparin can also be determined in another fashion. For example, it is possible to implement quantification of immobilised heparin using toluidine blue which binds to immobilised heparin.

Both methods lead to the same result.

RESULT OF EXAMPLE 1/COMPARATIVE EXAMPLES 1

TABLE 1

Table 1 shows the relative content of free amino acid residues (related to 1000 amino acid residues) in pig aortic valve vela

| Amino acid | Native tissue | GA | DEE + heparin | Example of the invention |
|---|---|---|---|---|
| THR | 27.3 ± 0.2 | 27.6 ± 0.6 | 24.5 ± 0.3 | 23.3 ± 0.5 |
| SER | 45.3 ± 0.4 | 46.7 ± 1.1 | 41.6 ± 0.4 | 39.6 ± 0.4 |
| GLU | 97.7 ± 0.0 | 103.0 ± 0.5 | 89.1 ± 0.7 | 88.2 ± 1.2 |

TABLE 1-continued

Table 1 shows the relative content of free amino acid residues
(related to 1000 amino acid residues) in pig aortic valve vela

| Amino acid | Native tissue | GA | DEE + heparin | Example of the invention |
|---|---|---|---|---|
| OHPRO | 110.4 ± 1.2 | 117.6 ± 1.2 | 115.6 ± 3.9 | 110.8 ± 1.8 |
| PRO | 25.7 ± 0.5 | 28.6 ± 0.4 | 65.6 ± 0.6 | 64.8 ± 1.7 |
| GLY | 238.2 ± 1.2 | 252.1 ± 4.1 | 261.1 ± 2.4 | 272.7 ± 3.2 |
| ALA | 124.3 ± 0.9 | 127.7 ± 0.8 | 122.3 ± 0.5 | 132.2 ± 3.1 |
| VAL | 44.3 ± 0.8 | 41.9 ± 1.2 | 42.0 ± 1.7 | 37.1 ± 1.4 |
| MET | 10.7 ± 0.3 | 10.6 ± 0.2 | — | — |
| ILE | 19.9 ± 0.3 | 20.2 ± 0.3 | 16.0 ± 0.3 | 16.7 ± 0.5 |
| LEU | 42.4 ± 0.3 | 42.6 ± 0.6 | 36.2 ± 0.3 | 36.1 ± 0.5 |
| TYR | 10.4 ± 0.3 | 9.4 ± 0.2 | 8.7 ± 0.2 | 1.9 ± 0.5 |
| PHE | 21.9 ± 0.4 | 20.9 ± 0.4 | 22.6 ± 0.7 | 19.7 ± 1.4 |
| HIS | 12.9 ± 0.2 | 15.8 ± 0.3 | 35.6 ± 0.4 | 39.2 ± 0.6 |
| OHLYS | 11.0 ± 0.2 | 1.4 ± 0.2 | 2.3 ± 0.2 | — |
| LYS | 34.0 ± 0.3 | 3.3 ± 0.2 | 7.4 ± 0.2 | — |
| ASP | 66.5 ± 0.5 | 70.0 ± 0.5 | 61.2 ± 0.5 | 60.1 ± 0.9 |
| ARG | 57.1 ± 0.8 | 63.1 ± 1.2 | 47.8 ± 0.9 | 56.3 ± 1.3 |

It is known that epoxide compounds react with methionine, tyrosine, lysine and hydroxylysine of the biological material, whereas glutaraldehyde reacts only with the last two amino acids. The results demonstrated confirm this.

In this respect when using the conserving agent according to the invention the density of transverse cross-linking is greater than when using the individual substance—ethylene glycol diglycidylether. That can be seen in particular from a reduction in the relative content of the amino acids methionine, tyrosine, lysine and hydroxylysine.

TABLE 2

Table 2 shows the physical-mechanical parameters of pig aortic valve vela conserved with various methods.

| Conserving agent | σ[kg/cm²] | ε[%] | h[cm] |
|---|---|---|---|
| Glutaraldehyde (GA) | 59.2 ± 4.6 | 38.7 ± 1.9 | 0.059 ± 0.003 |
| DEE + heparin | 69.9 ± 5.9 | 38.7 ± 1.8 | 0.046 ± 0.002 |
| Example of the inv. | 93.5 ± 8.0 | 35.9 ± 1.6 | 0.041 ± 0.002 |

Comments:
σ: breaking stress under tensile loading,
ε: relative stretch,
h: tissue thickness.

The sample produced according to the example of the invention, with a smaller thickness, has a better tensile strength characteristic (greater breaking stress).

TABLE 3

Table 3 shows the amount of calcium (mg/g of dry tissue) in valve vela portions implanted under the skin of rats at various periods after implantation.

| Implantation period | GA | DEE + heparin | Example of the inv. |
|---|---|---|---|
| Without implantation | 2.25 ± 0.10 | 2.18 ± 0.08 | 2.23 ± 0.11 |
| 30 days | 125.6 ± 10.2 | 2.5 ± 0.07 | 2.15 ± 0.08 |
| 60 days | 211.7 ± 12.4 | 2.8 ± 0.10 | 2.3 ± 0.07 |
| 90 days | 265.4 ± 21.3 | 2.5 ± 0.09 | 2.7 ± 0.11 |

The sample produced in accordance with the example of the invention has an extremely low degree of calcification.

TABLE 4

Table 4 shows the amount of immobilised heparin.

| DEE + heparin | Example according to the invention |
|---|---|
| 530 ± 20 μg/g dry tissue | 2340 ± 120 μg/g dry tissue |

The sample produced in accordance with the example of the invention has a very high content of immobilised heparin.

EXAMPLE 2 ACCORDING TO THE INVENTION

Segments of the internal thoracic artery of a pig (25 g of moist tissue) were rinsed with 0.9% by weight NaCl solution and put into 200 ml of a conserving solution which is produced from 50 mM HEPES-buffer pH 7.4 and contains 8 g of ethylene glycol diglycidylether, 0.5 g of polyethylene glycol diglycidylether (n=6) and 1.5 g of pentaerythrol polyglycidylether (number of glycidylether units per molecule: 4).

After 48 hours the conserving solution was replaced by an identical but freshly produced solution. After 12 days the segments were rinsed with sterile 0.9% by weight NaCl solution and incubated in a heparin solution (100 IU/ml) pH 5.0, wherein the pH-value was adjusted by the addition of aqueous acetylsalicylic acid solution (production, see Example 1 according to the invention), for a period of 4 hours at a temperature of 20° C. Production of the heparin solution was effected as described in Example 1.

Thereafter the segments were rinsed three times with an excess of 0.9% by weight NaCl solution and put into a 5% by weight ethylene glycol diglycidylether solution, where they were stored until further use.

COMPARATIVE EXAMPLES 2

The comparative samples used were segments of the internal thoracic artery of a pig, which were treated with 0.625% by weight glutaraldehyde in 50 mM phosphate buffer pH 7.4 (GA) and with 5% by weight ethylene glycol diglycidylether and 100 IU/ml heparin in 50 mM phosphate buffer pH-value 7.4 (DEE+heparin) (see RU 2 008 767). Production of the comparative samples was effected in accordance with the description set forth in relation to comparative Examples 1.

RESULT EXAMPLE 2/COMPARATIVE EXAMPLES 2

The operation of determining the density of transverse cross-linking, the degree of calcification and the amount of immobilised heparin was effected as described hereinbefore in relation to Example 1. The results contained in Example 1 and comparative Examples 1 are confirmed by the results obtained in the present case.

The resistance to thrombosis formation was assessed after the implantation of vessel segments which were conserved in accordance with the method according to the invention (example according to the invention) or for comparison purposes using glutaraldehyde (GA) or ethylene glycol diglycidylether and heparin (DEE+heparin), into the carotid artery of dogs.

In that case the vessel segments were between about 3 mm and 3.5 mm in diameter and between about 5 and 7 cm in length and were implanted in the neck artery (carotid) of 24 non-thoroughbred dogs which weighed between 10 and 15 kg.

The dogs were previously anethetised by the intravenous administration of sodium thiopental and mechanically ventilated. A carotid artery segment of between 5 and 7 cm in length was removed from the dogs and the bioprosthesis was implanted in place thereof using 6–0 polypropylene suture material.

Eight animals received a 'GA' bioprosthesis in the right carotid artery and a 'DEE+heparin' prosthesis in the left carotid artery; eight further animals received a 'DEE+heparin' bioprosthesis in the right carotid artery and a bioprosthesis according to the invention in the left carotid artery; eight further animals received a bioprosthesis according to the invention in the right carotid artery and a 'GA' prosthesis in the left carotid artery. The through-flow in the prostheses was examined prior to closure of the wound by means of pulsation palpation. The penetration capability of the bioprostheses was determined by means of angiography and ultrasound methods (Doppler echography, duplex scanning).

Evaluation of the data obtained was effected by means of actuarial analysis. Actuarial analysis is a standardised statistical procedure which is based on the probability of analysed complications, in the present case thrombosis, in which respect events which have already occurred are taken into consideration. Evaluation of the results was effected with the program STATISTICA for Windows (StatSoft, Inc, 1995).

BRIEF DESCRIPTION OF THE DRAWING

The actuarial values in respect of penetration capability in [%] of biological prostheses implanted in the neck artery (carotid) of the dogs were determined and are set forth in Table 5. The values specified in Table 5 are shown in graph form in FIG. 1.

TABLE 5

Figure 1:
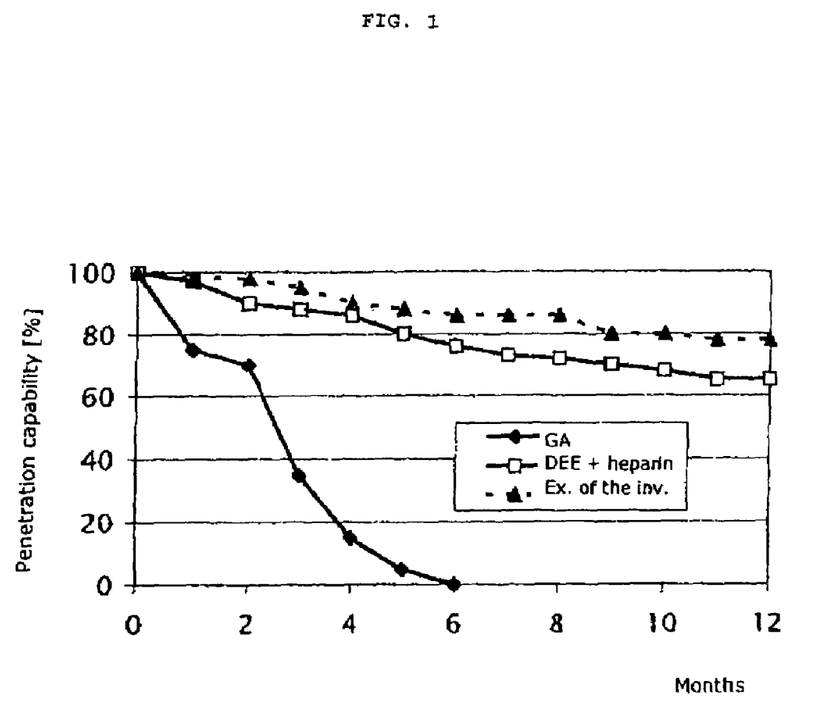

Table 5 shows the actuarial values of penetration capability of implanted bioprostheses in [%].

| Period in months | GA | DEE + heparin | Example of the inv. |
|---|---|---|---|
| 0 | 100% | 100% | 100% |
| 1 | 75% | 97% | 98% |
| 2 | 70% | 90% | 98% |
| 3 | 35% | 88% | 95% |
| 4 | 15% | 86% | 90% |
| 5 | 5% | 80% | 88% |
| 6 | 0% | 76% | 86% |
| 7 | | 73% | 86% |
| 8 | | 72% | 86% |
| 9 | | 70% | 80% |
| 10 | | 68% | 80% |
| 11 | | 65% | 78% |
| 12 | | 65% | 78% |

TABLE 6

Table 6 shows the relative content of free methionine, tyrosine, lysine and hydroxylysine residues (related to 1000 amino acid residues) in samples of the internal thoracic artery of a pig.

| Amino acid | Native tissue | GA | DEE + heparin | Ex. of the inv. |
|---|---|---|---|---|
| MET | 7.5 ± 0.5 | 7.3 ± 0.4 | 6.3 ± 0.2 | — |
| TYR | 10.0 ± 0.6 | 11.0 ± 0.4 | — | 3.4 ± 0.5 |
| OHLYS | 7.0 ± 0.5 | 1.0 ± 0.2 | 0.9 ± 0.2 | — |
| LYS | 24.1 ± 1.9 | 3.5 ± 0.5 | — | — |

TABLE 7

Table 7 shows the amount of immobilised heparin.

| DEE + heparin | Example according to the invention |
|---|---|
| 190 ± 10 µg/g dry tissue | 1005 ± 90 µg/g dry tissue |

TABLE 8

Table 8 shows the amount of calcium (mg/g of dry tissue) in samples implanted under the skin of rats of the internal thoracic artery of a pig at various periods after implantation.

| Implantation period | GA | DEE + heparin | Ex. of the inv. |
|---|---|---|---|
| Without implantation | 1.39 ± 0.11 | 1.5 ± 0.03 | 1.42 ± 0.09 |
| 30 days | 52.6 ± 4.1 | 1.35 ± 0.04 | 1.5 ± 0.10 |
| 60 days | 74.1 ± 9.3 | 1.8 ± 0.07 | 1.9 ± 0.07 |
| 90 days | 92.0 ± 10.4 | 1.5 ± 0.04 | 1.5 ± 0.01 |

EXAMPLE 3 ACCORDING TO THE INVENTION

Pig pericardium (30 g of moist tissue) was mechanically cleaned of the surrounding tissue, rinsed with 0.9% by weight NaCl solution and incubated in 200 ml of a conserving solution which is produced from 50 mM HEPES-buffer pH 7.4 and contains 4.5 g of ethylene glycol diglycidylether, 1.5 g of polyethylene glycol diglycidylether (n=4) and 4 g of pentaerythrol polyglycidylether (number of the glycidylether units per molecule: 4).

After 48 hours the solution was replaced by an identical abut freshly produced solution. After 12 days the pericardium was rinsed with sterile 0.9% by weight NaCl solution and incubated in a heparin solution (100 IU/ml) pH 6.0, wherein the pH-value was adjusted by the addition of aqueous acetylsalicylic acid solution (production, see Example 1 according to the invention), for a period of 4 hours at a temperature of 20° C.

Thereafter the pericardium was rinsed three times with an excess of 0.9% by weight NaCl solution and put into a 5% by weight ethylene glycol diglycidylether solution, where it was stored until further use.

COMPARATIVE EXAMPLES 3

The comparative samples used were pig pericardium portions which were treated with 0.625% by weight glutaraldehyde in 50 mM phosphate buffer pH 7.4 (GA) or with 5% by weight ethylene glycol diglycidylether (DEE) and 100 IU/ml heparin in 50 mM phosphate buffer pH-value 7.4 (DEE+heparin) (see RU 2 008 767). Production of the comparative samples was effected in accordance with the description set forth in relation to comparative Examples 1.

The operation of determining the density of transverse cross-linking, the properties in respect of elasticity and deformation and the amount of immobilised heparin was effected as described in Example 1. The results obtained in Example 1 and comparative Examples 1 are confirmed by the results obtained in the present case.

RESULT OF EXAMPLE 3 ACCORDING TO THE INVENTION/COMPARATIVE EXAMPLES 3

TABLE 9

Table 9 shows the relative content of free methionine, tyrosine, lysine and hydroxylysine residues (related to 1000 amino acid residues) in pig pericardia.

| Amino acid | native tissue | GA | DEE + heparin | Ex. of the inv. |
|---|---|---|---|---|
| MET | 8.8 ± 0.5 | 8.7 ± 0.5 | 4.4 ± 0.3 | — |
| TYR | 8.2 ± 0.2 | 8.0 ± 0.4 | — | 5.0 ± 0.3 |
| OHLYS | 9.9 ± 0.4 | 1.1 ± 0.1 | 0.7 ± 0.2 | 1.5 ± 0.1 |
| LYS | 32.0 ± 1.9 | 2.8 ± 0.1 | — | 1.4 ± 0.3 |
| ARG | 55.6 ± 0.8 | 58.6 ± 0.5 | 50.9 ± 0.8 | 12.7 ± 0.3 |

TABLE 10

Table 10 shows the amount of immobilised heparin.

| DEE + heparin | Example according to the invention |
|---|---|
| 760 ± 10 µg/g dry tissue | 2640 ± 85 µg/g dry tissue |

TABLE 11

Table 11 shows the physical-mechanical parameters of pig pericardium portions conserved with various methods.

| Conserving agent | σ [kg/cm²] | ε [%] | h [cm] |
|---|---|---|---|
| Glutaradehyde | 119.8 ± 6.2 | 48.5 ± 5.8 | 0.046 ± 0.003 |
| DEE + heparin | 123.3 ± 11.4 | 58.4 ± 3.5 | 0.044 ± 0.004 |
| Ex. of the inv. | 125.5 ± 12.3 | 57.0 ± 3.6 | 0.045 ± 0.005 |

Comments:
σ: breaking strain under tensile loading,
ε: relative stretch,
h: tissue thickness.

What is claimed is:

1. A conserved biological prosthesis produced in accordance with a method comprising the following steps:
   (a) treating a biological prosthesis with a solution which contains a mixture of epoxide compounds which are at least in part of different lengths, wherein said mixture of epoxide compounds includes at least one non-polymer epoxide compound with two epoxide groups;
   (b) treating the biological prosthesis treated in accordance with step (a) with a solution containing an antithrombotic, wherein the antithrombotic is a mixture of heparin and acetylsalicylic acid; and
   (c) optionally storing the prosthesis treated in accordance with step (b) in a sterilizing solution.

2. A conserved biological prosthesis as set forth in claim 1 wherein the biological prosthesis is selected from the group consisting of heart valves, artery segments, vein valves, valve-containing vein segments, and membranous tissues of a mammal.

3. The prosthesis as set forth is claim 2 wherein said prosthesis is a membranous tissue of a mammal.

4. The prosthesis as set forth in claim 3 wherein said membranous tissue is the pericardium of a mammal.

5. The prosthesis as set forth in claim 3 wherein said membranous tissue is the meninges of a mammal.

6. The prosthesis as set forth in claim 1 wherein the solution of step (a) contains a mixture of at least three different epoxide compounds.

7. The prosthesis as set forth in claim 1 wherein the mixture of epoxide compounds further includes at least one polymer epoxide compound with two or three epoxide groups and/or an epoxide compound with two or three epoxide groups, wherein arranged between at least two epoxide groups is a straight-chain or branched hydrocarbon chain with at least four carbon atoms.

8. The prosthesis as set forth in claim 1 wherein the mixture of epoxide compounds includes at least one epoxide compound with at least three epoxide groups.

9. The prosthesis as set forth in claim 1 wherein the epoxide group is a component of a glycidol residue.

10. The prosthesis as set forth in claim 1 wherein said at least one non-polymer epoxide compound is selected from the group which consists of alkylene glycol diglycidylethers, alkane diol diglycidylethers, polyalcohol diglycidylethers, and mixtures thereof.

11. The prosthesis as set forth in claim 10 wherein said at least one non-polymer epoxide compound is an alkylene glycol diglycidylether.

12. The prosthesis as set forth in claim 11 wherein said alkylene glycol diglycidylether is ethylene glycol diglycidylether.

13. The prosthesis as set forth in claim 10 wherein said at least one non-polymer epoxide compound is an alkane diol diglycidylether.

14. The prosthesis as set forth in claim 13 wherein said alkane diol diglycidylether is butane-1,4 diol diglyciceylether.

15. The prosthesis as set forth in claim 10 wherein said at least one non-polymer epoxide compound is a polyalcohol diglycidylether.

16. The prosthesis as set forth in claim 15 wherein said polyalcohol diglycidylether is glycerine diglycidylether.

17. The prosthesis as set forth in claim 1 wherein the polymer epoxide compound is a polyalkylene glycol glycidylether.

18. The prosthesis as set forth in claim 17 wherein said polyakylene glycol glycidylether is selected from the group consisting of polyethylene glycol diglycidylether, polytetramethylene glycol glycidylether, polypropylene glycol diglycidylether, and mixtures thereof.

19. The prosthesis as set forth in claim 1 wherein the non-polymer epoxide compounds is/are alkane diol diglycidylether, and/or dicarboxylic acid diglycidylester.

20. The prosthesis as set forth in claim 19 wherein said non-polymer epoxide compound is hexane-1,6-diol-diglycidylether.

21. The prosthesis as set forth in claim 8 wherein the epoxide compounds with at least three epoxide groups are selected from the group which consists of polyalcohol polyglycidylethers, glycerine polyglycidylether, pentaerythrol polyglycidylether, polysaccharide polyglycidylether, and mixtures thereof.

22. The prosthesis as set forth in claim 21 wherein said epoxide compound with at least three epoxide groups is a polyalcolhol polyglycidylether.

23. The prosthesis as set forth in claim 22 wherein said polyalcohol polyglycidylether is sorbitol polyglycidylether.

24. The prosthesis as set forth in claim 1 wherein after the treatment in accordance with step (a) in step (b) the biological prosthesis is treated with a solution of heparin and acetylsalicylic acid without using additional reagents.

25. The prosthesis as set forth in claim 24 wherein after the treatment with heparin and acetylsalicylic acid in accordance with step (b) the biological prosthesis is rinsed in distilled water or an isotonic solution, in particular a 0.9% by weight NaCl solution, and then sterilized by treatment with a solution of an epoxide compound.

26. The prosthesis as set forth in claim 25 wherein the solution used for sterilization has a concentration of the epoxide compound of at least 2% by weight.

* * * * *